United States Patent [19]
Moore et al.

[11] Patent Number: 5,991,979
[45] Date of Patent: Nov. 30, 1999

[54] SKIN MOUNTED DEVICE HOLDER

[75] Inventors: Patricia A. Moore, Incline, Nev.;
David A. Sheraton, Irvine, Calif.

[73] Assignee: Alpine Partners, Incline Village, Nev.

[21] Appl. No.: 08/939,136

[22] Filed: Sep. 29, 1997

[51] Int. Cl.⁶ .................................................. A44B 21/00
[52] U.S. Cl. ................................................ 24/306; 24/304
[58] Field of Search .............................. 24/3.1, 306, 304,
24/DIG. 11; 248/205.2, 205.3; 224/901,
901.2; 604/180; 128/DIG. 15

[56] References Cited

U.S. PATENT DOCUMENTS

| | | |
|---|---|---|
| 3,288,137 | 11/1966 | Lund . |
| 3,834,380 | 9/1974 | Boyd . |
| 4,702,736 | 10/1987 | Kalt et al. . |
| 4,755,173 | 7/1988 | Konopka et al. . |
| 4,898,587 | 2/1990 | Mera ................................... 604/180 X |
| 5,037,397 | 8/1991 | Kalt et al. ............................ 604/180 X |
| 5,147,322 | 9/1992 | Bowen et al. . |
| 5,397,639 | 3/1995 | Tollini . |
| 5,447,492 | 9/1995 | Cartmell et al. . |
| 5,480,719 | 1/1996 | Tollini ................................. 604/180 X |

FOREIGN PATENT DOCUMENTS

WO 86/06640  11/1986  WIPO .

*Primary Examiner*—James R. Brittain
*Attorney, Agent, or Firm*—Charles C. H. Wu

[57] ABSTRACT

A skin mounted device holder for holding generally medical devices such as fluid reservoirs. The skin mounted device holder includes a base member comprised of a resilient cloth material and having a VELCRO attached to its top surface and a water based adhesive material coated onto the bottom of its surface, a securing flap having a VELCRO for mating with the VELCRO of the base means, and a connector loop having an attachment for attaching medical devices. The connector loop loops around the securing strap and thus connects the medical devices to the base member.

10 Claims, 3 Drawing Sheets

SKIN MOUNTED DEVICE HOLDER

BACKGROUND OF THE INVENTION

The present invention relates to a skin mounted device holder for holding medical devices to a person's skin, and more particularly a securing tape in the form of a Velcro type of fastener for securing a reservoir such as for use in holding body fluid.

It is important that the skin mounted devices stick to human skin firmly because one of the most frequent applications of the skin mounted device holder is to hold fluid reservoirs in connection to a woman's mastectomy. In addition, the skin mounted device holder when constructed with hydrogel is easily removable without causing tear of the skin. This is especially important to patients who have already endured painful medical procedures and one less pain would certainly assist in patients' recovery.

It is also important that the means for attaching the reservoirs be easily releasable so that the reservoirs can be quickly drained out and be remounted again.

One of the purposes of the present invention is to replace a tower type of hanger for hanging fluid reservoirs. Therefore, patients need not carry around a bulky tall hanger that restricts patients' mobility.

A need therefore exists for an inexpensive skin mounted device holder for medical patients, especially mastectomy patients.

The present invention provides an economical means to meet the aforesaid everyday common medical requirements.

SUMMARY OF THE INVENTION

The present invention provides an economical medical device holder for attaching and mounting body fluid reservoirs and the like devices onto a patient's skin. It further can provide a reusable and non-painful method of removing the device holder apart from the patient's skin when constructed with hydrogel.

For ease of presentation, this section describes the skin mounted device holder on a horizontal plane. Other orientations are possible and this description is not intended to limit the scope of the invention to any particular geometry of the elements.

The present invention meets the requirements of quick mounting of medical fluid reservoirs, quick releases of medical devices, and a re-usable adhesive strip of tape for attaching onto a person's skin. The present invention provides a resilient base means having a water based adhesive on one side for adhering to a patient's skin and a VELCRO type of fastening material on the other side for allowing a securing flap to be secured onto the base means. The base means has sufficient flexibility such that it will adopt to the movements and flexibility of a patient's skin and muscle rather than breaking the contact between the base means and the patient's skin.

The adhesive is of a hydrogel type, commonly available in the medical industry. The hydrogel is composed of medical grade material. Three possible manufacturers of the hydrogel are Energy Technology, Promeon and Lectec.

The base means with the medical grade hydrogel adhesive can be mounted to any part of a patient's body due to the unique nature of the hydrogel. Unlike a typical adhesive, the hydrogel can be easily peeled off the skin of a patient.

A connector loop is looped around the securing flap for securing onto the base means. Medical devices such as body fluid drain reservoirs are attached to the connector loop and thus follow the patient around.

The base means having a hydrogel release adhesive liner attaches to the surface of the adhesive. The hydrogel adhesive release liner protects the adhesive to prevent accidental sticking of the adhesive during the preparation and shipping of the skin mounted device holder.

BRIEF DESCRIPTION OF THE DRAWINGS

These and other features, aspects, and advantages of the present invention will become better understood with reference to the following description, appended claims, and accompanying drawings, where:

DESCRIPTION OF THE PREFERRED EMBODIMENT

The present invention is directed to a device for providing a means for attaching medical devices onto patients' skin. The medical devices suitable for this application are fluid reservoirs.

Figure 2:
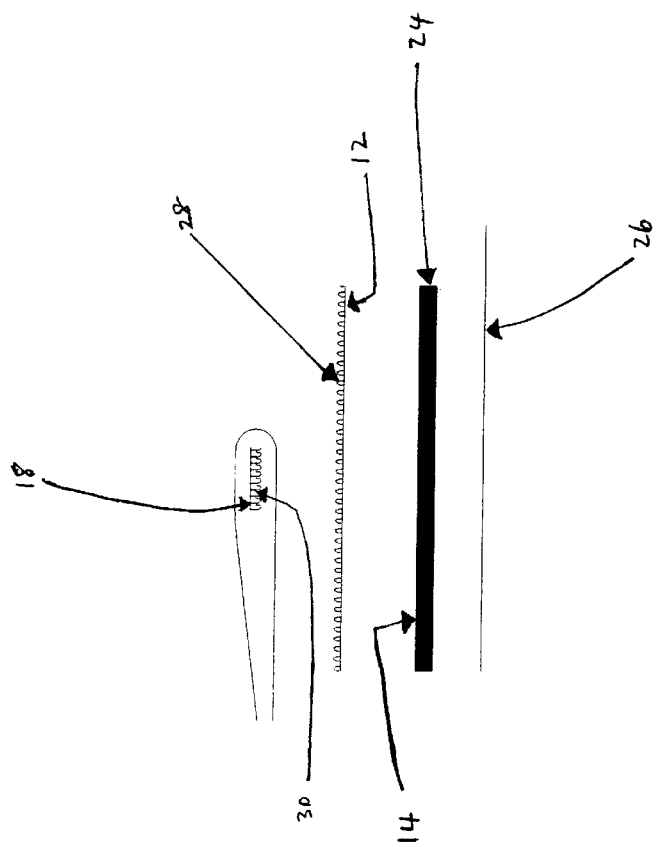
FIG. 2 is a side view of the Skin Mounted Device Holder according to the present invention attached to a typical reservoir loop.
Figure 1:
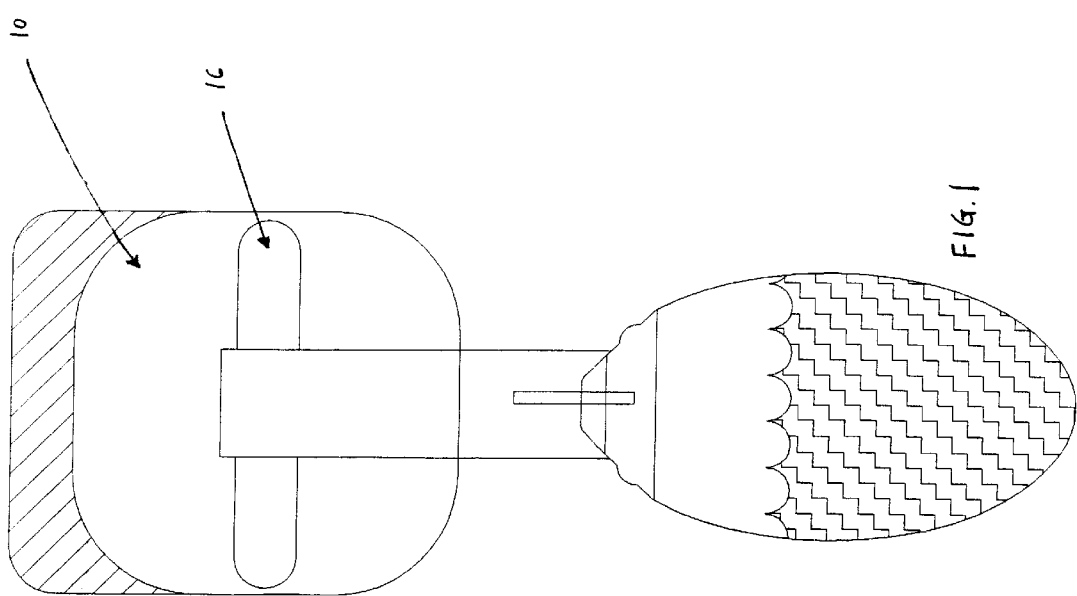
FIG. 1 is a horizontal view of the Skin Mounted Device Holder according to the present invention depicting an attachment to a typical reservoir.
Figure 3:
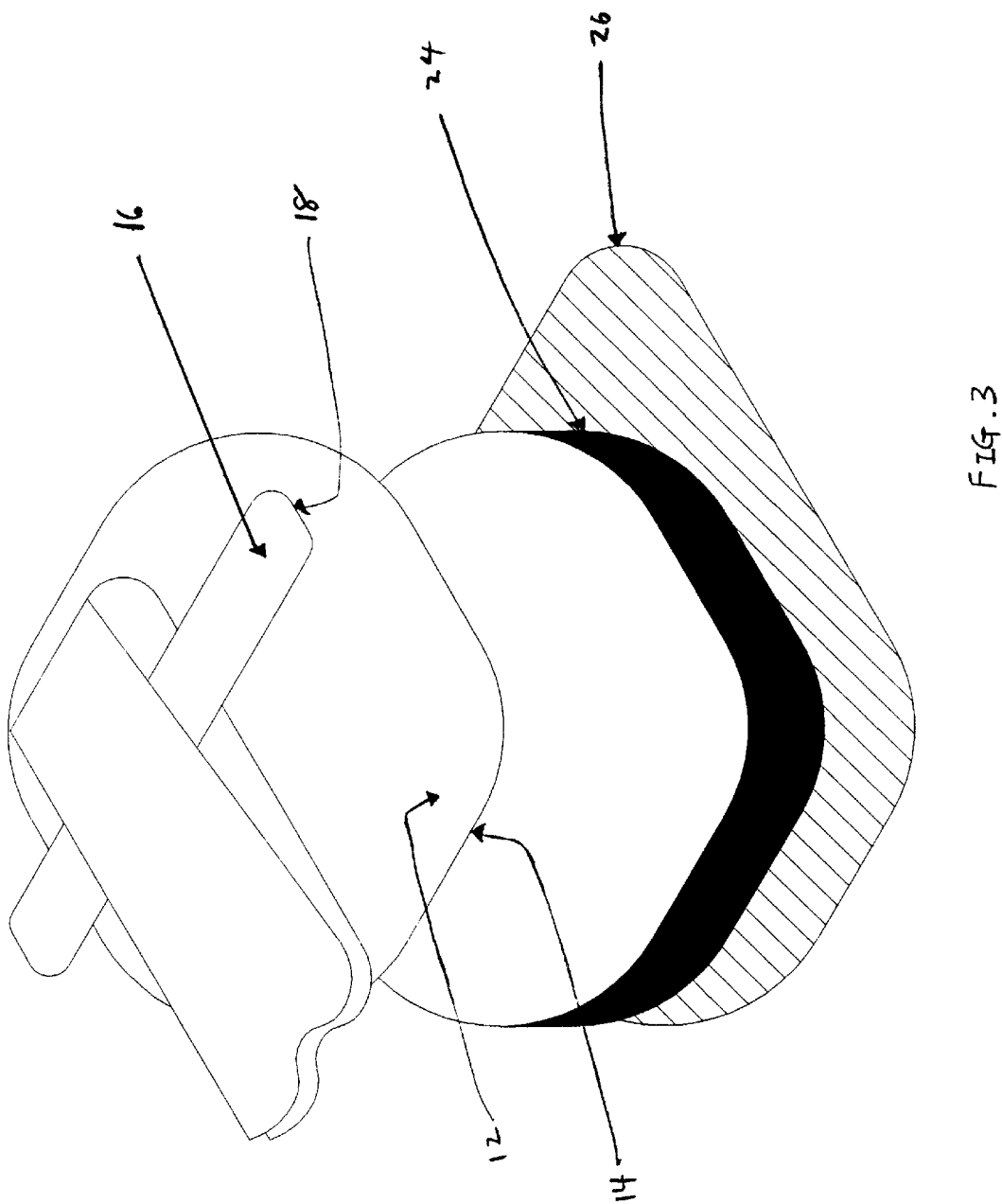
FIG. 3 is an angular side view of the Skin Mounted Device Holder according to the present invention securing a typical reservoir loop.
Figure 4:
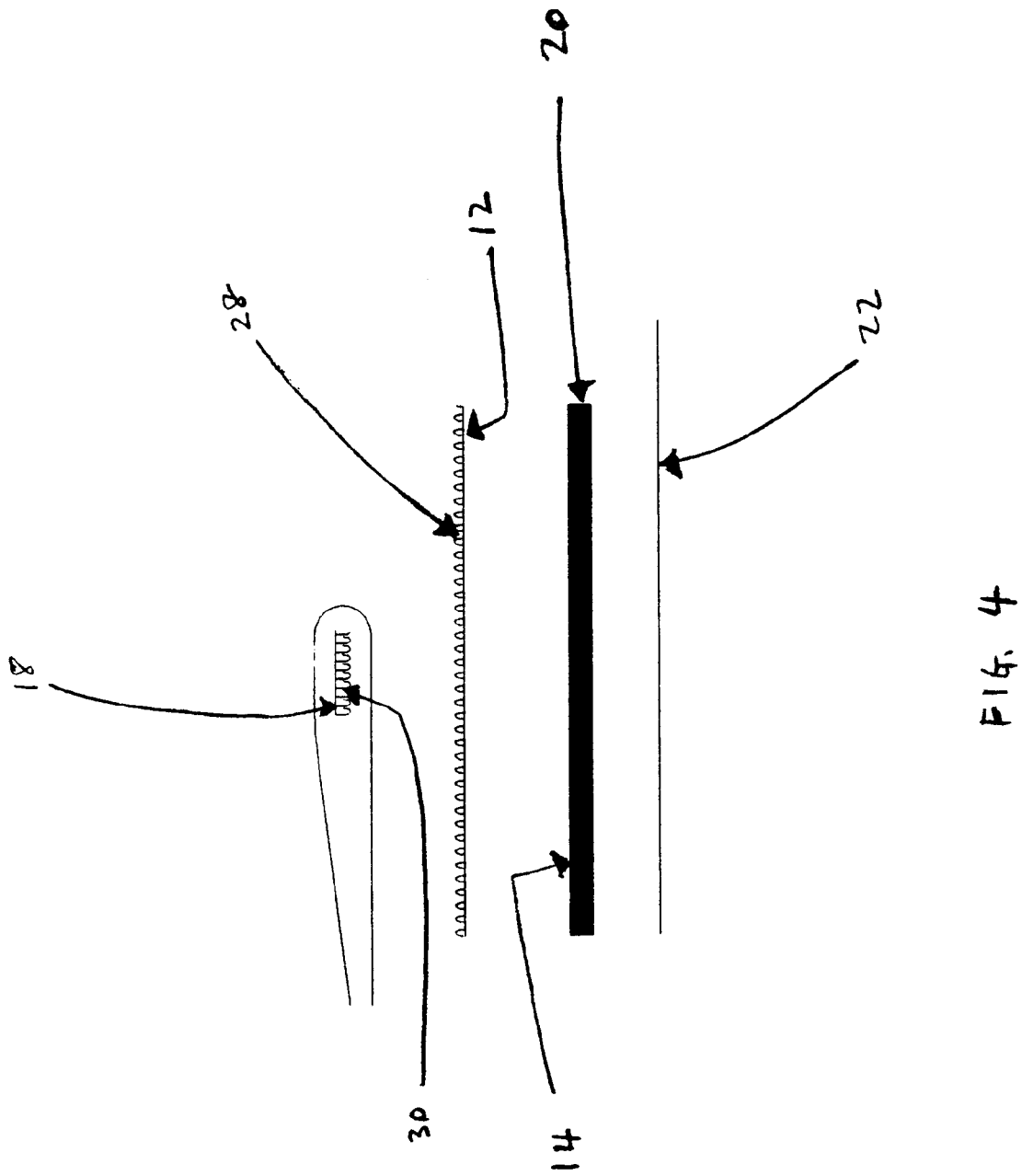
FIG. 4 is a version of the invention utilizing a pressure sensitive adhesive.

With reference to FIGS. 1–3 of the drawings, a base means 10 having a top surface 12 and further having a bottom surface 14. The base means top surface 12 includes a first fastening means 28 which is woven onto the top surface 12 of the base means 10. A preferred fastening means of the first fastening means 28 is a VELCRO type of loop or pile fastening material. The bottom surface 14 of the base means 10 is coated with a hydrogel adhesive 24 such as the types available from Energy Technology, Promeon and Lectec. Those skilled in the art will understand that any other material suitable for similar medical applications may also be used.

A hydrogel adhesive release liner 26 is adhered to the hydrogel adhesive 24. During application, the hydrogel adhesive release liner 26 is peeled away from the hydrogel adhesive 24 and exposing the hydrogel adhesive 24 for adhering to the skin of a patient.

Securing flap 16 having a bottom surface 18 is adopted for attaching onto the top surface 12 of base means 10. The bottom surface 14 of the securing flap 16 includes a second fastening means 30 which is woven onto the securing flap bottom surface 18. A preferred fastening means of the second fastening means 30 is a VELCRO type of hook material. Attachment of the securing flap 16 is provided through the mating of the second fastening means 30 attached to the bottom surface 18 of the securing flap 16 to the first fastening means 28 of the top surface 12 of the base means 10.

A connector loop 20 having two ends. One end is wrapped around the securing flap 16 for extending down from the securing flap 16. A medical device attachment means 22 is attached to the other end of the connector loop 20 opposite to the end wrapping around the securing flap 16. As best seen in FIG. 1, the securing loop 20 extends down from the securing flap 16 and connects to medical devices such as body fluid reservoirs via the medical device attachment means 22. It will be understood by those skilled in the art that the design of the connector loop 20 allows securing flap 16 to be used as a means to attach medical devices onto the human skin.

Although the present invention has been described in considerable detail with reference to certain preferred versions thereof, other versions are possible. For example, the first fastening means 28 may comprised of a VELCRO type of hook fastening material and the second fastening means 30 may comprised of a VELCRO type of pile or loop material. In addition, the first fastening means 28 and the second fastening means 30 can be fasteners similar to the VELCRO type but do not necessarily need to be VELCRO.

Therefore, the spirit and scope of the appended claims should not necessarily be limited to the description of the preferred version contained herein.

What is claimed is:

1. A skin mounted device holder comprising:
   (a) base means having a top surface and a bottom surface, said top surface having a first fastening means woven onto said top surface, said bottom surface coated with an adhesive for adhering to human skin;
   (b) a securing flap having a bottom portion, said bottom portion having a second fastening means woven into said bottom portion for mating to said first fastening means;
   (c) the first fastening means is adapted to mate with the second fastening means;
   (d) a connector loop having a first end and a second end, the first end loops around the securing flap, the second end having an attachment means for attaching medical devices; and
   (e) an adhesive release liner adhering to the adhesive and to be peeled away and thereby exposing the adhesive.

2. The skin mounted device holder of claim 1, wherein the base means comprises a resilient pad of cloth material.

3. The skin mounting device holder of claim 1, wherein the first fastening means is loop material.

4. The skin mounting device of claim 1, wherein the second fastening means is hook material.

5. A skin mounted device holder for holding body fluid reservoir comprising:
   (a) base means having a top surface and a bottom surface, said top surface having a first fastening means woven onto said top surface, said bottom surface coated with adhesive for adhering to human skin;
   (b) a securing flap having a bottom portion said bottom portion having a second fastening means woven into said bottom portion for mating to said first fastening means;
   (c) the first fastening means is adapted to mate with the second fastening means;
   (d) a connector loop having a first end and a second end, the first end loops around the securing flap, the second end having an attachment means for attaching medical devices; and
   (e) an adhesive release liner adhering to the adhesive and to be peeled away and thereby exposing the adhesive.

6. The skin mounted device holder of claim 5, wherein the base means comprises a resilient pad of cloth material.

7. The skin mounting device holder of claim 5, wherein the adhesive is comprised of hydrogel.

8. The skin mounting device holder of claim 5, wherein the first fastening means is hook material.

9. The skin mounting device of claim 5, wherein the second fastening means is loop material.

10. A skin mounted device holder for holding body fluid reservoirs comprising:
    a base means having a top surface and a bottom surface, the base means comprises a resilient cloth material, said top surface having a first fastening means comprised of loop material woven onto said top surface, said bottom surface coated with adhesive for adhering to human skin, said adhesive is comprised of hydrogel;
    a securing flap having a bottom portion said bottom portion having a second fastening means comprised of hook material woven into said bottom portion for mating to said first fastening means;
    a connector loop having a first end and a second end, the first end loops around the securing flap, the second end having an attachment means for attaching medical devices;
    the first fastening means is adapted to mate with the second fastening means; and
    an adhesive release liner adhering to the adhesive and to be peeled away and thereby exposing the adhesive.

* * * * *